(12) United States Patent
Lee et al.

(10) Patent No.: US 11,244,427 B2
(45) Date of Patent: Feb. 8, 2022

(54) IMAGE RESOLUTION PROCESSING METHOD, SYSTEM, AND APPARATUS, STORAGE MEDIUM, AND DEVICE

(71) Applicant: TENCENT TECHNOLOGY (SHENZHEN) COMPANY LIMITED, Guangdong (CN)

(72) Inventors: Huai Che Lee, Shenzhen (CN); Kai Wei Chen, Shenzhen (CN); Jhih Rong Chen, Shenzhen (CN)

(73) Assignee: TENCENT TECHNOLOGY (SHENZHEN) COMPANY LTD, Shenzhen (CN)

( * ) Notice: Subject to any disclaimer, the term of this patent is extended or adjusted under 35 U.S.C. 154(b) by 0 days.

(21) Appl. No.: 16/918,175

(22) Filed: Jul. 1, 2020

(65) Prior Publication Data
US 2020/0334790 A1    Oct. 22, 2020

Related U.S. Application Data

(63) Continuation of application No. PCT/CN2019/075519, filed on Feb. 20, 2019.

(30) Foreign Application Priority Data

Apr. 27, 2018   (CN) .......................... 201810392834.X

(51) Int. Cl.
 *G06T 3/40* (2006.01)
 *G06T 5/00* (2006.01)
(52) U.S. Cl.
 CPC ............ *G06T 3/4053* (2013.01); *G06T 5/003* (2013.01)

(58) Field of Classification Search
None
See application file for complete search history.

(56) References Cited

U.S. PATENT DOCUMENTS

2004/0160458 A1\*  8/2004  Igarashi .............. G06F 3/04855
                                                              345/660
2014/0361977 A1   12/2014  Stafford et al.
(Continued)

FOREIGN PATENT DOCUMENTS

CN         105392538 A        3/2016
CN         108596834 A        9/2018

OTHER PUBLICATIONS

International Search Report for PCT/CN2019/075519 dated May 24, 2019 [PC/ISA/210].
(Continued)

*Primary Examiner* — Aaron M Richer
(74) *Attorney, Agent, or Firm* — Sughrue Mion, PLLC

(57) ABSTRACT

An image resolution processing method includes: obtaining motion information of a display apparatus; determining a motion direction and rate information of the display apparatus according to the motion information; determining, according to the motion direction, a target object that is at least one of a horizontal resolution and a vertical resolution; determining a target value according to the rate information and a standard resolution of the display apparatus; and generating a to-be-displayed image, a value of the target object in an image resolution of the to-be-displayed image being equal to the target value.

18 Claims, 11 Drawing Sheets

(56) References Cited

U.S. PATENT DOCUMENTS

| | | | |
|---|---|---|---|
| 2015/0348493 A1* | 12/2015 | Chae | G09G 5/00 345/212 |
| 2016/0131908 A1* | 5/2016 | Fateh | G06F 3/016 345/633 |
| 2016/0147063 A1 | 5/2016 | Border et al. | |
| 2016/0170488 A1 | 6/2016 | Hanamoto | |
| 2017/0206625 A1* | 7/2017 | Fainstain | G06T 1/20 |
| 2018/0075654 A1 | 3/2018 | Vembar et al. | |
| 2018/0286004 A1* | 10/2018 | Babu | G06F 3/011 |

OTHER PUBLICATIONS

Extended European Search Report dated Dec. 22, 2021 in European Application No. 19792700.7.

* cited by examiner

IMAGE RESOLUTION PROCESSING METHOD, SYSTEM, AND APPARATUS, STORAGE MEDIUM, AND DEVICE

CROSS-REFERENCE TO THE RELATED APPLICATION(S)

This application is a bypass continuation application of International Application No. PCT/CN2019/075519, filed Feb. 20, 2019, which claims priority to Chinese Patent Application No. 201810392834.X, entitled "IMAGE RESOLUTION PROCESSING METHOD, IMAGE PROCESSING APPARATUS AND SYSTEM, AND STORAGE MEDIUM" filed with the China National Intellectual Property Administration on Apr. 27, 2018, which is incorporated herein by reference in its entirety.

FIELD

Examine embodiments of the disclosure relate to the field of image processing technologies, and in particular, to an image resolution processing method, and a system, an apparatus, a storage medium, and a device related to an image resolution processing.

BACKGROUND

With the development of electronic technologies and computer technologies, a user may obtain or generate various images and process and display various images according to requirements, to meet an image visual requirement. For example, in the field of virtual reality (VR) or augmented reality (AR), related image processing such as making some special images or rendering is involved, to finally display processed images on a display apparatus such as VR/AR glasses, helmets, and the like, to provide a satisfactory visual experience to the user.

In a system such as VR/AR, during display of an image, for example, during display of a game image, it is usually required to maintain an image refresh rate higher than a certain image refresh rate threshold, for example, an image refresh rate of 90 fps (frames per second). Maintaining the refresh rate is an important factor to ensure the image visual experience of the user. Therefore, a method of ensuring a certain refresh rate becomes an important issue and much research has been conducted.

SUMMARY

Example embodiments of the disclosure provide an image resolution processing method, system, and apparatus, a storage medium, and a device, in which a certain image refresh rate and an image visual experience of a user are ensured.

According to an aspect of an example embodiment, an image resolution processing method includes:
  obtaining motion information of a display apparatus;
  determining a motion direction and rate information of the display apparatus according to the motion information;
  determining, based on the motion direction, a target object that is at least one of a horizontal resolution and a vertical resolution;
  determining a target value according to the rate information and a standard resolution of the display apparatus; and
  generating a to-be-displayed image, a value of the target object in an image resolution of the to-be-displayed image being equal to the target value.

According to an aspect of an example embodiment, an image resolution processing system includes an image processing device and a display apparatus, where
  the image processing device is configured to: obtain motion information of the display apparatus; determine a motion direction and rate information of the display apparatus according to the motion information; determine, according to the motion direction, a target object that is at least one of a horizontal resolution and a vertical resolution; determine a target value according to the rate information and a standard resolution of the display apparatus; generate a to-be-displayed image, a value of the target object in an image resolution of the to-be-displayed image being equal to the target value; and output a target image according to the to-be-displayed image; and
  the display apparatus is configured to: transmit the motion information to the image processing device, and display the target image after receiving the target image.

According to an aspect of an example embodiment, an image resolution processing apparatus includes:
  at least one memory configured to store program code; and
  at least one processor configured to read the program code and operate as instructed by the program code, the program code comprising:
    obtaining code configured to cause at least one of the at least one processor to obtain motion information of a display apparatus, and determine a motion direction and rate information of the display apparatus according to the motion information;
    determining code configured to cause at least one of the at least one processor to determine, according to the motion direction, a target object that is at least one of a horizontal resolution and a vertical resolution;
    calculating code configured to cause at least one of the at least one processor to determine a target value according to the rate information and a standard resolution of the display apparatus; and
    generating code configured to cause at least one of the at least one processor to generate a to-be-displayed image, a value of the target object in an image resolution of the to-be-displayed image being equal to the target value.

According to an aspect of an example embodiment, a non-volatile computer-readable storage medium stores computer-readable instructions, the computer-readable instructions, when executed by one or more processors, causing the one or more processors to perform the following operations:
  obtaining motion information of a display apparatus;
  determining a motion direction and rate information of the display apparatus according to the motion information;
  determining, according to the motion direction, a target object that is at least one of a horizontal resolution and a vertical resolution;
  determining a target value according to the rate information and a standard resolution of the display apparatus; and
  generating a to-be-displayed image, a value of the target object in an image resolution of the to-be-displayed image being equal to the target value.

According to an aspect of an example embodiment, an image processing device includes a memory and a processor, the memory storing computer-readable instructions, and the computer-readable instructions, when executed by the processor, causing the processor to perform the following operations:

obtaining motion information of a display apparatus;

determining a motion direction and rate information of the display apparatus according to the motion information;

determining, according to the motion direction, a target object that is at least one of a horizontal resolution and a vertical resolution;

determining a target value according to the rate information and a standard resolution of the display apparatus; and generating a to-be-displayed image, a value of the target object in an image resolution of the to-be-displayed image being equal to the target value.

BRIEF DESCRIPTION OF THE DRAWINGS

To describe the technical solutions of the example embodiments of the disclosure or the related art more clearly, the following briefly introduces the accompanying drawings required for describing the example embodiments or the related art. Apparently, the accompanying drawings in the following description show only some embodiments of the disclosure, and a person of ordinary skill in the art may still derive other drawings from these accompanying drawings without creative efforts.

DETAILED DESCRIPTION

Figure 1:
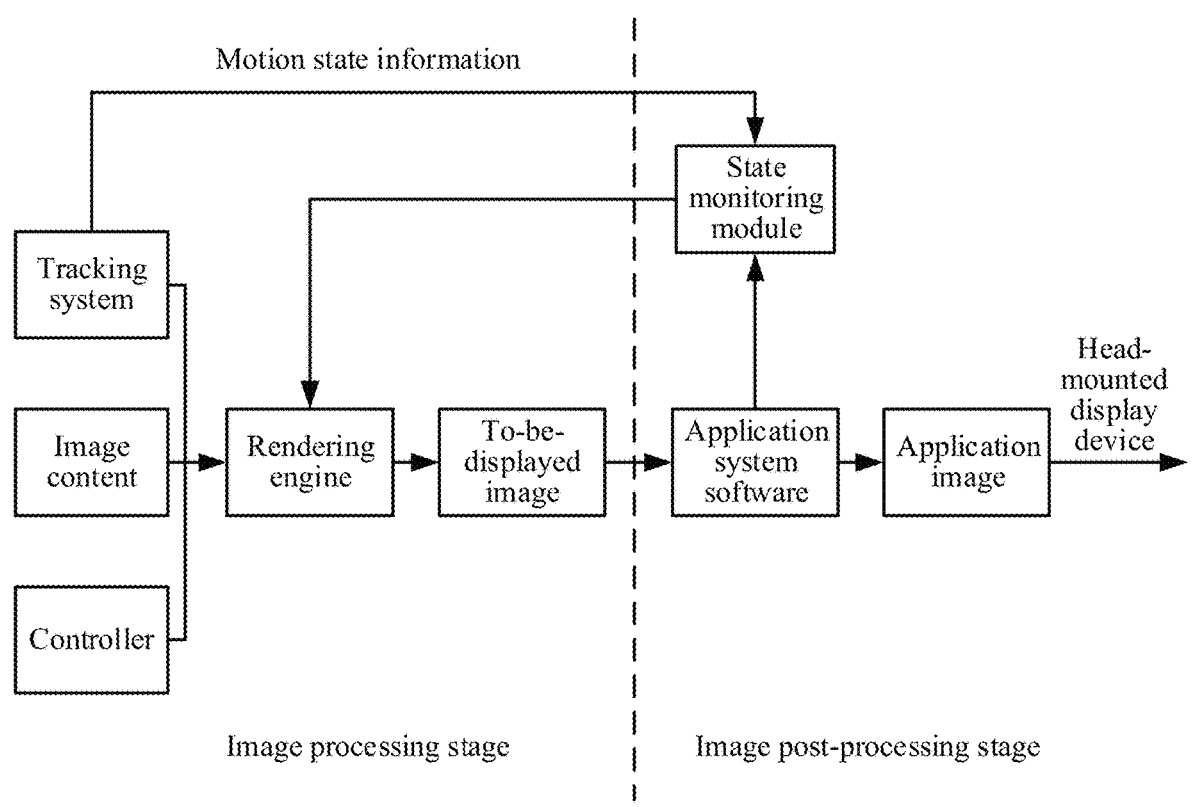
FIG. 1 is a schematic diagram of an image processing procedure according to an example embodiment of the disclosure.

The technical solutions in the example embodiments of the disclosure will be clearly and completely described in the following with reference to the accompanying drawings in the example embodiments of the disclosure.

Terms including ordinal numbers, such as "first," "second," etc., may be used to represent various elements, but do not limit the elements. The terms are only used for distinguishing one element from another element. For example, a first element may also be called a second element, and similarly, the second element may also be called the first element without departing from the scope of the disclosure. As used herein, the term "and/or" includes any and all combinations of one or more of the associated listed items. Expressions such as "at least one of," when preceding a list of elements, modify the entire list of elements and do not modify the individual elements of the list.

To ensure a certain image refresh rate, and further ensure an image visual experience of a user to a certain extent, comfort of the user when viewing an image in a head-mounted display apparatus is researched, and it is found that, when the entire body or head of the user is in a still state or a low-speed motion state, attention of human eyes on a fine structure of the image outperforms refresh rate performance. That is, during slight motion of a user, the user pays more attention to an image resolution and whether the image is clear. On the contrary, when the entire body or head moves rapidly, human eyes cannot clearly see details in a scene image actually, but are more sensitive to the fluency of the image, that is, the image refresh rate. That is, to enhance a user's visual experience, during vigorous motion of the user, the refresh rate may be improved, and the resolution may be reduced. Therefore, in a process of generating a to-be-displayed image in an example embodiment of the disclosure, motion information (e.g., information such as a displacement velocity, displacement acceleration, a motion angle, a motion angular velocity, and motion angular acceleration) is introduced as a basis for regulating a resolution value. By reducing the resolution value in a motion direction during rapid motion, a finally generated to-be-displayed image may be blurred in a certain degree, and the generated blur may be closer to an effect of visual persistence.

In an example embodiment of the disclosure, when a user displays various images by using augmented reality (AR) glasses, a virtual reality (VR) helmet or other types of display apparatuses, in a process of generating a to-be-displayed image, an image resolution may be dynamically adjusted by monitoring a motion state of the user. By using an original standard resolution as a reference, the image resolution is reduced to a target resolution, and the to-be-displayed image is generated according to the target resolution. Thus, the image resolution is adjusted. Specifically, a value of a horizontal resolution and/or a vertical resolution in the standard resolution is adjusted, to reduce a corresponding value, so that a computation amount of image rendering is reduced to achieve a higher image refresh rate, thereby ensuring that when the user uses a display apparatus such as VR glasses and is in an image viewing scene, a game playing scene or the like, an image processing device may perform processing such as image rendering in time. The fluency of images is ensured, and immersion is improved for the user. The user does not feel discomfort such as dizziness even in a moving process.

Figure 2:
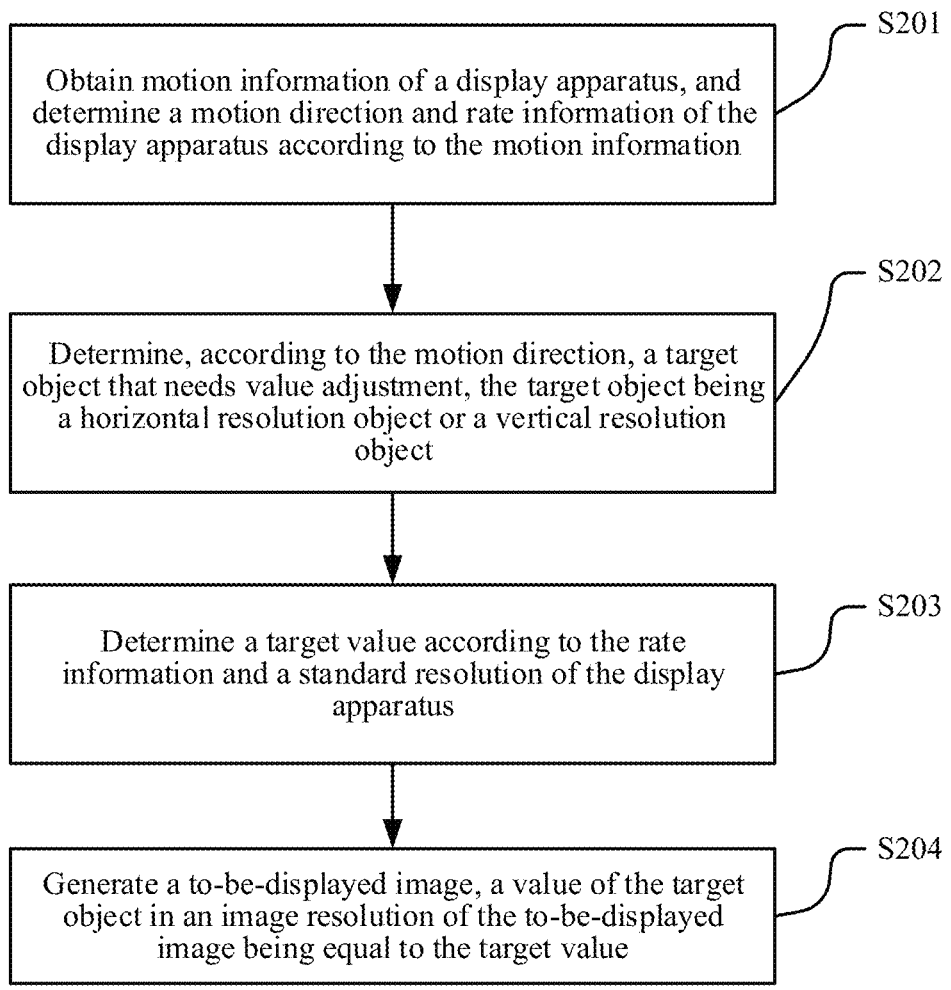
FIG. 2 is a schematic flowchart of an image resolution processing method according to an example embodiment of the disclosure.

FIG. 1 is a schematic diagram of an image processing procedure according to an example embodiment of the disclosure. The image processing procedure includes an image processing stage and an image post-processing stage. The image processing stage mainly includes processing such as image rendering to generate a to-be-displayed image. The image post-processing mainly processes the to-be-displayed image into an image that may be displayed by a display apparatus. For example, in a VR application scenario, in the image processing stage, processing is mainly performed based on a game engine or the like, to obtain a to-be-displayed game image, and in the image post-processing stage, the to-be-displayed image is processed to obtain a game image that may be correctly displayed in VR glasses. FIG. 2 is a schematic flowchart of an image resolution processing method according to an example embodiment of the disclosure. The following describes an image processing procedure in an example embodiment of the disclosure in detail with reference to FIG. 1 and FIG. 2.

Content data in FIG. 1 refers to date such as original image content and game content, and a controller may be, for example, a key controller for controlling an image, a game object, or the like. The controller controls an image playback mode or motion of an object in a game by transmitting a control instruction. The image processing device performs image processing by using a rendering engine. The rendering engine may be, for example, various types of game engines. On one hand, the content data and the instruction transmitted by the controller are combined by a rendering engine, to perform basic processing such as logic processing, controlling, and image rendering. On the other hand, determining of a target object and calculation of a target value are performed based on a motion direction of the display apparatus. The image processing device synthesizes a result of the basic processing and the target value obtained through calculation to generate a to-be-displayed image. A value of the to-be-displayed image on the target object (e.g., a horizontal resolution and/or a vertical resolution) is the target value. In this embodiment of the disclosure, it is defined that an image resolution includes two objects. The two objects may be the horizontal resolution and the vertical resolution. The two objects at different image resolutions have respective values. For example, when a standard resolution is 1920×1080, a value of the horizontal resolution corresponding to the standard resolution may be 1920, and a value of the vertical resolution may be 1080.

In an example embodiment, after the to-be-displayed image is obtained in the image processing stage, the to-be-displayed image is processed by application system software to obtain an application image that may be directly displayed on the head-mounted display device. The application image is directly displayed by a display module of the head-mounted display device. The display module may directly display the application image by using a display screen, or the application image may be displayed in another manner, such as projection display by a projection apparatus.

In an example embodiment, the image resolution processing method includes the following operations S201-S204:

S201. Obtain motion information of a display apparatus, and determine a motion direction and rate information (e.g., information of a motion rate such as a speed) of the display apparatus according to the motion information.

S202. Determine, according to the motion direction, a target object that needs value adjustment, the target object being a horizontal resolution and/or a vertical resolution.

S203. Determine a target value according to the rate information and a standard resolution of the display apparatus.

S204. Generate a to-be-displayed image, a value of the target object in an image resolution of the to-be-displayed image being equal to the target value.

In an example embodiment, in a process of calculating the target value by the image processing device based on the motion direction, first, in operation S201, the motion information of the display apparatus is obtained, and the motion direction and the rate information of the display apparatus are determined according to the motion information. In an embodiment, the image processing device may determine a current motion direction of the display apparatus by using a tracking system shown in FIG. 1. Specifically, the motion information of the display apparatus may be detected by using a sensor such as an acceleration sensor, a gyro sensor, or the like disposed on the display apparatus. The motion information may be, for example, three-axis rotation state information (including an angle/an angular velocity/angular acceleration), and/or position state information (including a position/a speed/acceleration) of the display apparatus. The current motion direction of the display apparatus may be determined based on the motion information. For example, the motion information may include the motion direction.

In operation S202, the image processing device determines, according to the motion direction of the display apparatus, a target object that needs value adjustment, the target object being a horizontal resolution and/or a vertical resolution. As described above, the motion direction is determined according to the motion information. That is, a value of the horizontal resolution may be reduced according to a requirement, or a value of the vertical resolution is reduced, or both values of the horizontal and vertical resolutions are reduced. The image processing device may preset a mapping relationship between motion directions and coordinate axes in a pixel coordinate system. In an embodiment, the image processing device may create a correspondence between a motion direction during motion in a horizontal direction and a horizontal coordinate axis in the pixel coordinate system. That is, the value of the horizontal resolution may be reduced during motion in the horizontal direction. The image processing device may create a correspondence between a motion direction during motion in a vertical direction and a vertical coordinate axis in the pixel coordinate system. That is, the value of the vertical resolution may be reduced during motion in the vertical direction. For diagonally upward motion or diagonally downward motion, the motion may be split into two components: horizontal motion and vertical motion. A motion direction of the component in the horizontal direction may correspond to a decrease in the horizontal resolution. A motion direction of the component in the vertical direction may correspond to a decrease in the vertical resolution.

In an embodiment, after the target object is determined, the image processing device may further determine the rate information of the display apparatus according to the motion information of the display apparatus. In an embodiment, the motion information includes current angular velocity information, angular acceleration information, displacement velocity information, displacement acceleration information, and the like of the display apparatus. The motion information may be determined by obtaining motion data sensed on the three axes from a motion sensor such as an acceleration sensor, and/or a gyroscope.

After the motion information is obtained, in operation S203, the image processing device determines the target value according to the rate information of the display apparatus and the standard resolution of the display apparatus. The rate information is also determined according to the motion information. The standard resolution refers to a pre-configured resolution in a rendering engine. If the motion of the display apparatus is not considered, the rendering engine performs image processing according to the standard resolution to obtain the to-be-displayed image with the standard resolution. Generally, a resolution of the display apparatus is used as the standard resolution. For example, if the resolution of the display apparatus is 1920×1080, the standard resolution is 1920×1080. After the target value is obtained, the to-be-displayed image may be generated in S204 based on the target value. The value of the target object in the image resolution of the to-be-displayed image is the target value. That is, if the display apparatus moves in the horizontal direction, the value of the standard resolution on the horizontal resolution is subsequently adjusted. If the display apparatus moves in the vertical direction, the value of the standard resolution on the vertical resolution is subsequently adjusted. For example, when the standard resolution is 1080×1200 and no motion is detected, a to-be-displayed image with a resolution of 1080×1200 is to be outputted; if motion in the horizontal direction is detected, a to-be-displayed image with a resolution of 583×1200 may be outputted. That is, the value on the horizontal resolution is adjusted from 1080 to a target value 583. If the motion in the vertical direction is detected, a to-be-displayed image with a resolution of 1080×1080 is outputted. That is, the value on the vertical resolution is adjusted from 1200 to a target value 1080. If a user has motion components in both the horizontal direction and the vertical direction, a to-be-displayed image with a resolution of 583×1080 may be outputted. That is, the target value is less than the value of the target object in the standard resolution, and the target value is determined according to the value of the target object in the standard resolution multiplied by a resolution ratio. The resolution ratio is a value greater than a lowest threshold and not greater than 1. The lowest threshold may be, for example, 0.4 or 0.5.

In an embodiment, the target value of the image resolution of the to-be-displayed image may be calculated by a state monitoring module in FIG. 1. The state monitoring module finally outputs optimized rendering format indication information by using an algorithm about a visual impact of a motion state according to information such as processing state information of the whole image processing process, the motion information of the display apparatus, the standard resolution information, and the like. The rendering format indication information includes a target value of one or two target objects, a Level of Details (LoD for short, which is a method of reducing three-dimensional (3D) object complexity), hierarchical geometric fineness regulation value, and the like. The state monitoring module may be a dedicated hardware module in a product, or may be a functional module implemented by a processor based on computer program instructions.

In an embodiment, the processing state information of the image processing process includes information such as a current processing duration and a current rendering resolution (that is, the standard resolution). The state monitoring module transmits the rendering format indication information to the rendering engine, and the rendering engine regulates the image resolution of the to-be-displayed image according to the rendering format indication information. That is, in an embodiment, S201 to S203 are performed by the dedicated state monitoring module disposed in the image processing device, and S204 is performed by the rendering engine in the image processing device. In an embodiment, both the state monitoring module and the rendering engine may be disposed in an image processing device. The image processing device may be, for example, a VR host device or an AR host device. The image processing device may alternatively be included in a wearable device having a host function and a display function. That is, the wearable device may include the image processing device and a display apparatus. The state monitoring module shown in FIG. 1 is in the image post-processing stage. It mainly means that the state monitoring module is an application-level function, or a part of the application system software. In another embodiment, there may be no state monitoring module. In this case, functions of the state monitoring module may be directly configured in the rendering engine.

The LoD method mentioned above is mainly used for reducing geometric fineness of some models in a compromise with the image refresh rate. That is, after the value of the target object in the standard resolution is adjusted to the target value (or while the value is adjusted), a target image object may be further determined, and the geometric fineness of the target image object is adjusted according to a geometric fineness adjustment rule. The determined target image object refers to an image object whose image area in the to-be-displayed image that needs to be finally outputted is less than an area threshold. In an embodiment, an adjustment process of the geometric fineness includes: pre-configuring a plurality of different geometric fineness models, or a dynamic control rule of the geometric fineness for each to-be-rendered object (image object). When rendering occurs each time, an image area occupied by the to-be-rendered object in the to-be-displayed image is calculated, and a corresponding geometric fineness model is determined according to the occupied image area, or the dynamic control rule of the geometric fineness is selected to control the geometric fineness of the to-be-rendered image. In the to-be-displayed image that reaches the target value through adjustment, the occupied area changes as the target resolution of the to-be-rendered image changes. Once an occupied area of an image object is less than a design threshold, for example, once occupied area pixels are less than ¼ of object geometric finesse (a ball area is four times a projected area), the image object is the target image object, and a model with lower first-order geometric fineness is directly used for the target image object during rendering, so that computation required by the rendering is reduced.

In another embodiment, the operation of determining the target value according to the rate information of the display apparatus determined according to the motion information and the standard resolution of the display apparatus may also be implemented simply by the rendering engine. After the tracking system obtains related motion information, the rendering engine may feed back the motion direction and the motion rate information obtained based on the motion information to the rendering engine. The rendering engine finally obtains the target value through calculation according to the standard resolution. The rendering engine may further finish adjustment processing of the geometric finesses mentioned above. That is, in an embodiment, S201 to S204 may be performed by the rendering engine of the image processing device. In an embodiment, the image processing device may be, for example, a VR host device or an AR host device, or may be an important component of a wearable device having a host function and a display function. That is, the wearable device may include the image processing device and a display apparatus.

Figure 3:
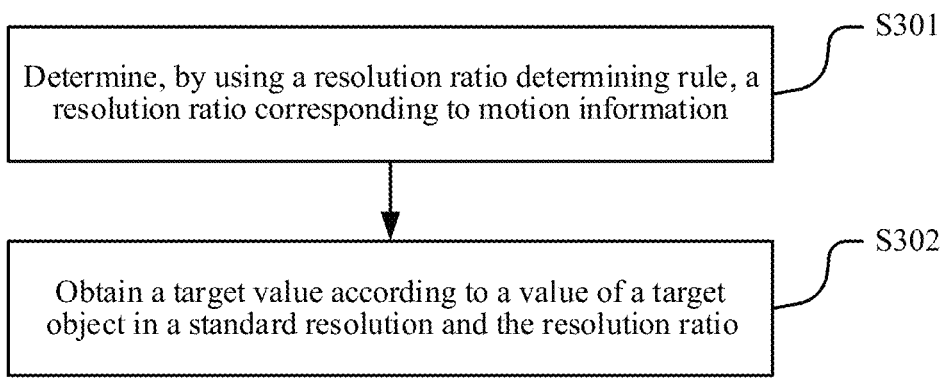
FIG. 3 is a schematic diagram of a calculation method of a target value according to an example embodiment of the disclosure.

FIG. 3 is a schematic diagram of a calculation method of a target value according to an example embodiment of the disclosure. Operation S203 mentioned above, that is, the operation of determining a target value according to the rate information of the display apparatus and a standard resolution of the display apparatus, the rate information being determined according to the motion information, specifically includes the following operations: Operation S301. Determine a resolution ratio corresponding to the motion information by using a resolution ratio determining rule. Operation S302. Obtain the target value according to the value of the target object of the standard resolution and the resolution ratio.

A motion speed may be in direct proportion to a degree of a blur that is visually acceptable. Therefore, in this embodiment of the disclosure, a relationship between the motion speed and the blur degree may be represented by a slope, and the slope may be determined according to the resolution ratio determining rule. In addition, considering that human eyes will track the object during slight motion, the resolution is not reduced when it is determined that the motion is low-speed motion in an example embodiment of the disclosure. During setting of the resolution ratio determining rule, the situation of not reducing the resolution in a low-speed case is also taken into consideration. In addition, lattice-like noise is generated when an image sampling rate is excessively low, and is easily noticed by the user. Therefore, an excessively low image sampling rate also needs to be avoided during setting of the resolution ratio determining rule.

Figure 4:
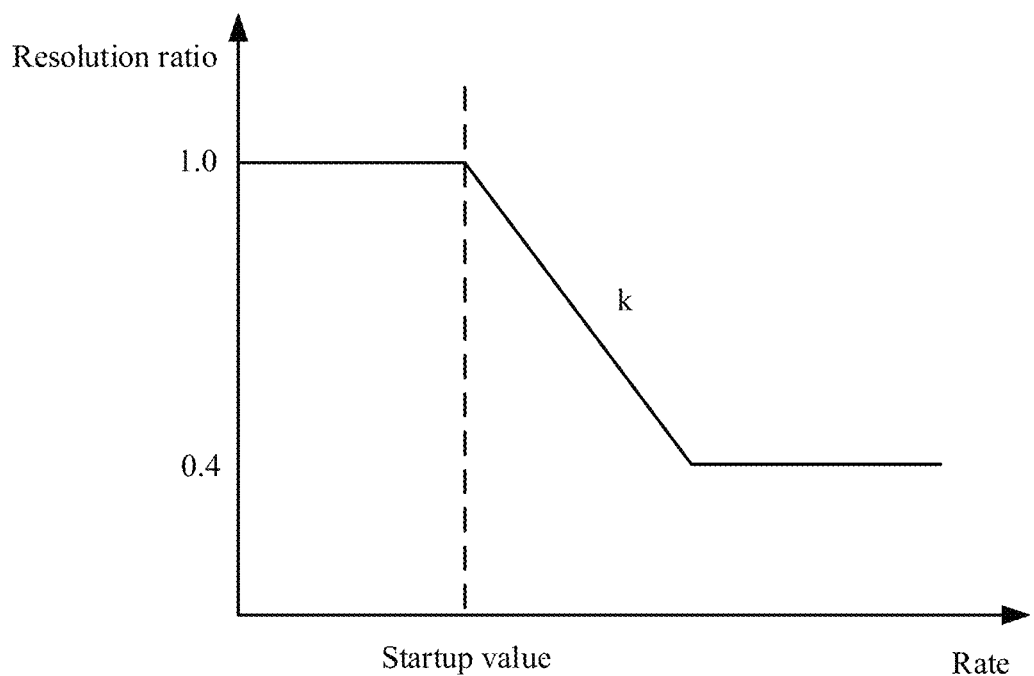
FIG. 4 is a schematic diagram of a resolution ratio determining rule according to an example embodiment of the disclosure.

Based on the foregoing, an actual adjustment manner may be shown in FIG. 4. FIG. 4 is a schematic diagram of a resolution ratio determining rule according to an example embodiment of the disclosure. Specific startup motion values (for example, a motion velocity value, an angular velocity value, an angular acceleration value, and the like) and the slope vary due to system performance of the image processing device. In an embodiment, to avoid the excessively low image sampling rate, a minimum reduction of the resolution value may be based on a ratio of 0.4 to 0.5. That is, a minimum resolution ratio is a value between 0.4 and 0.5. That is, it is defined in the resolution ratio determining rule that, if the motion value corresponding to the rate information is less than a first threshold, it is determined that the resolution ratio corresponding to the motion information is a first fixed ratio. If the motion value corresponding to the rate information is greater than a first threshold, it is determined that the resolution ratio a corresponding to the rate information is a=kb, where k is a slope, and b is a motion value (for example, a speed value) corresponding to the rate information. In addition, it is also defined in the resolution ratio determining rule that the resolution ratio is not less than a second fixed ratio.

For each image processing device with different performance, resolution ratios corresponding to different motion values may be determined by performing manual control on the image processing device, to manually calibrate the first threshold (that is, a startup value in FIG. 4) and the second fixed ratio (the second fixed ratio may be, for example, the ratio of 0.4 to 0.5 mentioned above) of the image processing device. The first fixed ratio may be, for example, 1, that is, the resolution value is not reduced. The slope k may be obtained through mathematical calculation such as straight line fitting based on a plurality of coordinate points (corresponding to the motion value and the resolution ratio) obtained between the first threshold and a value corresponding to the motion information during generating of the second fixed ratio. While a reference refresh rate (for example, 90 fps) is ensured, a plurality of coordinate points may be obtained comprehensively, via testing, based on acceptable degrees of an image blur in motion with respect to a plurality of users.

In an embodiment, resolution ratios of an image processing device under various motion values (or motion value ranges) may be directly obtained through manual testing, and a mapping relationship, for example, a mapping table, between the motion values (or the motion value ranges) and the resolution ratios is established. When operation S301 is subsequently performed, a resolution ratio in a mapping with the motion value corresponding to the motion information may be determined directly based on the mapping relationship.

Figure 5:
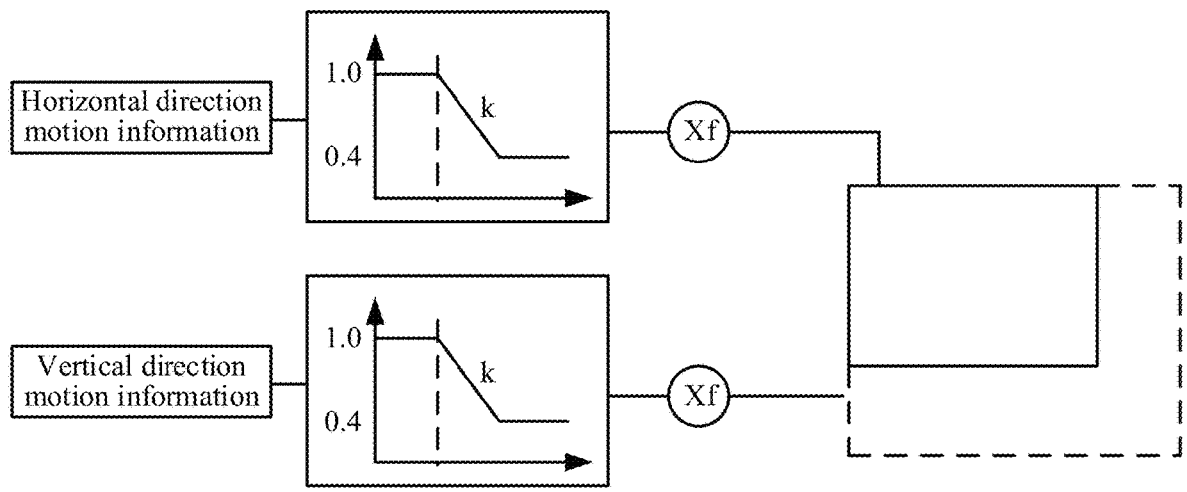
FIG. 5 is a schematic diagram of calculation of a target value according to an example embodiment of the disclosure.

FIG. 5 is a schematic diagram of calculation of a target value in an embodiment. A resolution ratio of an X direction (corresponding to the horizontal resolution) corresponding to horizontal direction motion information is denoted by Xf. A resolution ratio of a Y direction (corresponding to the vertical resolution) corresponding to vertical direction motion information is denoted by Yf. A target value in the X direction is equal to a value in the X direction in the standard resolution multiplied by Xf. A target value in the Y direction is equal to a value in the Y direction in the standard resolution multiplied by Yf. When motion exists in both the X direction and the Y direction, a relationship between the finally obtained target value and the standard resolution may be as shown in FIG. 5.

Figure 6:
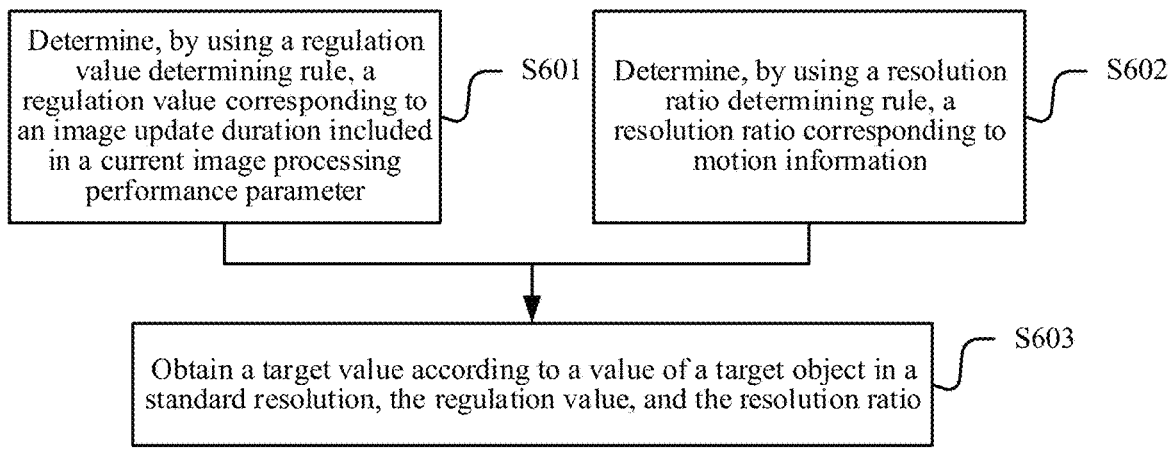
FIG. 6 is a schematic diagram of another calculation method of a target value according to an example embodiment of the disclosure.

In an embodiment, FIG. 6 is a schematic diagram of a calculation method of a target value according to another example embodiment of the disclosure. Operation S203 mentioned above, that is, the operation of determining a target value according to the rate information of the display apparatus and a standard resolution of the display apparatus specifically includes the following operations: S601. Determine, by using a regulation value determining rule, a regulation value corresponding to an image update duration (e.g., a duration taken for a single frame of an image to be updated) included in a current image processing performance parameter. S602. Determine, by using a resolution ratio determining rule, a resolution ratio corresponding to the motion information. S603. Obtain the target value according to a value of the target object in the standard resolution, the regulation value, and the resolution ratio. For specific implementation of S602, the description of example embodiments corresponding to FIG. 4 and FIG. 5 may be referred to.

Figure 7:
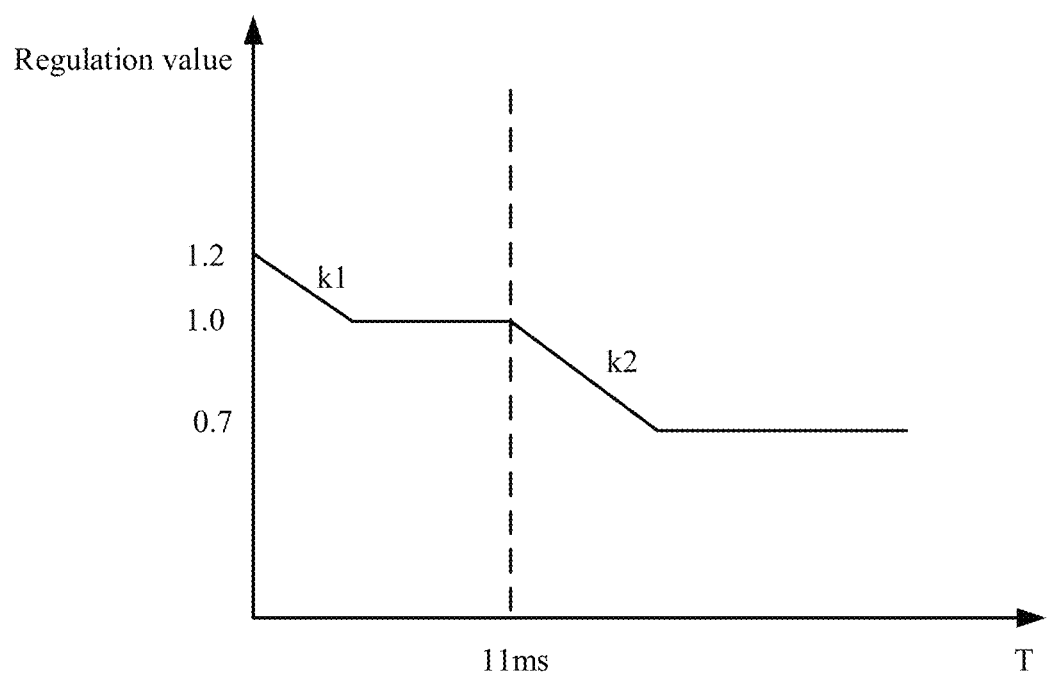
FIG. 7 is a schematic diagram of a relationship between a regulation value and a processing duration according to an example embodiment of the disclosure.

In this embodiment of the disclosure, the regulation value mentioned in S601 may be generated according to a duration of the current rendering processing, and is denoted by Gf. The value may be greater than 1.0 when a rendering time is short (for example, far less than 11 ms) to facilitate oversampling processing, thereby improving the resolution and enhancing picture details. The regulation value Gf is reduced when the rendering time is relatively long, thereby reducing the resolution. An example of a relationship between the regulation value Gf and the processing duration is illustratively shown in FIG. 7. That is, it is determined in the resolution ratio determining rule mentioned in S601 that: if the image update duration included in the current image processing performance parameter is less than a first duration threshold, the regulation value is determined to be a first fixed regulation value; in addition, the regulation value is not less than a second fixed regulation value. In an embodiment, the relationship between the regulation value Gf and the processing duration shown in FIG. 7 may also be obtained as follows: considering different performances of image processing devices, and determining the slope k1 and the slope k2 in FIG. 7 based on straight line fitting or the like. As shown in FIG. 7, the first fixed regulation value is 1.2, the second fixed regulation value is 0.7, and the first duration threshold is a duration value less than 11 ms, for example, 6 ms. It may be experimentally determined that, generally, the fluency of image displaying may be ensured as long as a refresh rate of 90 fps (frames per second) may be maintained, and 11 ms is approximately equal to 1/90. In other embodiments, the first duration threshold may alternatively be any other value. For example, if the refresh rate is required to be 60 fps, the first duration threshold may be 16.6 ms, or a similar value such as 16 ms. In an embodiment, the processing duration may refer to a total duration for completing processing of one frame of image in the above-mentioned two stages: the image processing stage and the image post-processing stage, and may be considered as a duration taken for a general process unit (GPU) to finish processing of a complete and directly displayable image. Time spent on each frame of image from the beginning of rendering to the final completion may be recorded by inquiring an operation state from the GPU, to obtain the processing duration. In other embodiments, a period of time may be defined by a test user as the processing duration, so as to better and more accurately determine the regulation value Gf.

Figure 8:
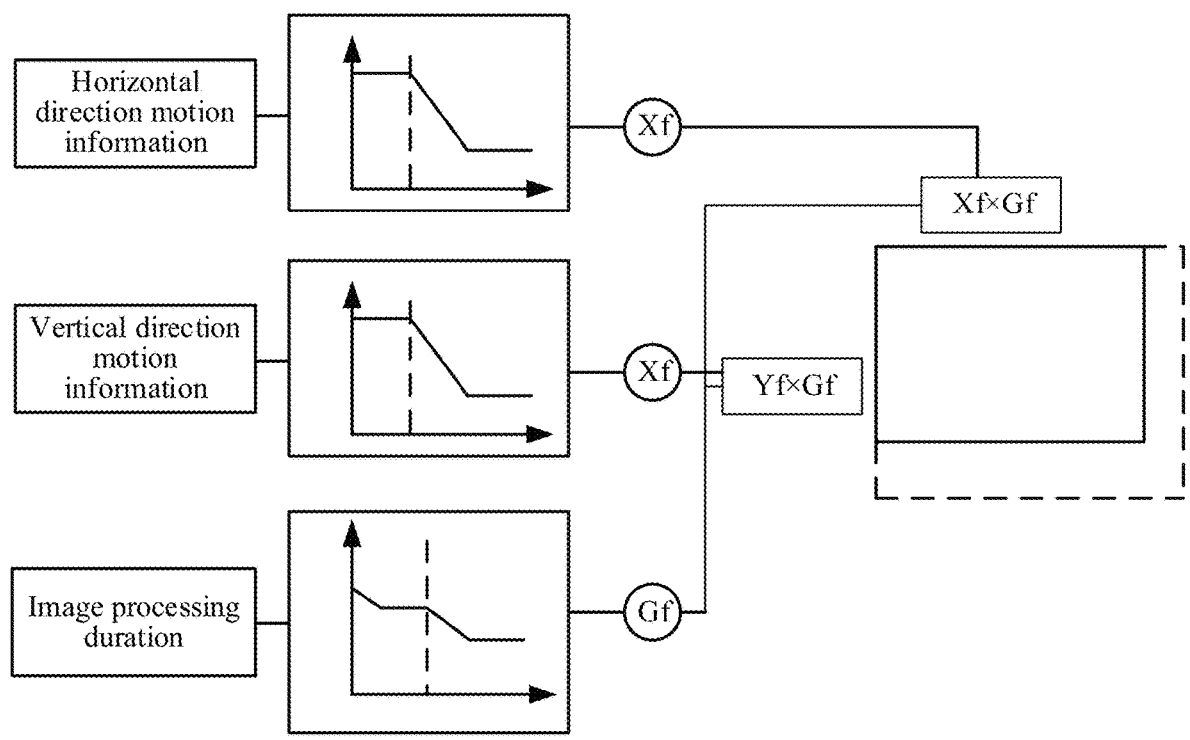
FIG. 8 is a schematic diagram of another calculation of a target value according to an example embodiment of the disclosure.

FIG. 8 is a schematic diagram of a calculation method of a target value in still another example embodiment. A resolution ratio of an X direction (corresponding to the horizontal resolution) corresponding to horizontal direction motion information is denoted by Xf. A resolution ratio of a Y direction (corresponding to the vertical resolution) corresponding to vertical direction motion information is denoted by Yf. A target value in the X direction is equal to a value in the X direction in the standard resolution multiplied by Xf and Gf. A target value in the Y direction is equal to a value in the Y direction in the standard resolution multiplied by Yf and Gf. When motion exists in both the X direction and the Y direction, a relationship between the finally obtained target value and the standard resolution may be as shown in FIG. 8.

For example, in an image processing device whose standard resolution is 1080×1200, when the image processing device requires a processing duration of 13 ms, a value corresponding to the corresponding regulation value Gf is 0.9. In this case, an action of turning the head quickly is performed in the X direction, and a resolution ratio Xf corresponding to a speed in the X direction is 0.6. Motion in the Y direction is slow motion, and the resolution ratio is 1.0. In this case, a target value in the X direction=1080×0.6× 0.9=583 (which may be rounded up in a rounding-off manner), and a target value in the Y direction=1200×1× 0.9=1080 may be obtained through calculation. Therefore, a suggested target value is 583×1080, and a pixel calculation amount is reduced by 51.4%. A rendering load may be greatly reduced by reducing the resolution ratio, so as to maintain the image fluency.

For the obtained to-be-displayed image whose image resolution on the target object is the target value, before the to-be-displayed image is displayed by the display apparatus, the to-be-displayed image may be magnified according to the display resolution of the display apparatus and the resolution of the to-be-displayed image, and the magnified to-be-displayed image is outputted to the display apparatus for display, so as to display the to-be-displayed image on the display apparatus in a full screen manner. In an embodiment, it may be specified that a size of a render target is a screen resolution size of the display apparatus, so that the GPU may automatically render a magnification result.

Figure 9:
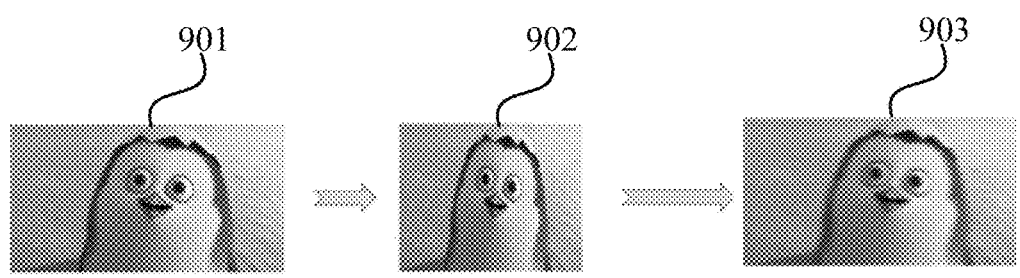
FIG. 9 is a schematic diagram of comparing images according to an example embodiment of the disclosure.

As shown in FIG. 9, an image 901 is a to-be-displayed image having a standard resolution that is to be originally outputted. However, after image resolution value processing (or adjustment), an image 902 is outputted, that is, a to-be-displayed image in which the value of the horizontal resolution in the X direction is adjusted to a corresponding target value. Before the image is outputted to the display apparatus for final display, that is, in the image post-processing stage mentioned above, the image 902 is magnified based on an actual display resolution of the display apparatus, and an image 903 is finally outputted to the display apparatus for display. The image 903 is blurred in a certain degree in the X direction. The magnification performed after the resolution value is reduced blurs the image. A pattern of the image blur is related to a direction in which the resolution value is reduced. For example, reducing the value in the X direction (that is, the horizontal resolution) causes a horizontal blur of the magnified image, and reducing the value in the Y direction (that is, the vertical resolution) causes a vertical blur of the magnified image.

In this embodiment of the disclosure, through the processing of reducing the resolution value in a known motion direction, a blur effect generated after the magnification coincides with the motion direction. This is in accordance with a visual effect. The image refresh rate may be effectively improved, thereby reducing negative impact on the image quality caused by the blur to a certain extent.

Figure 10A:
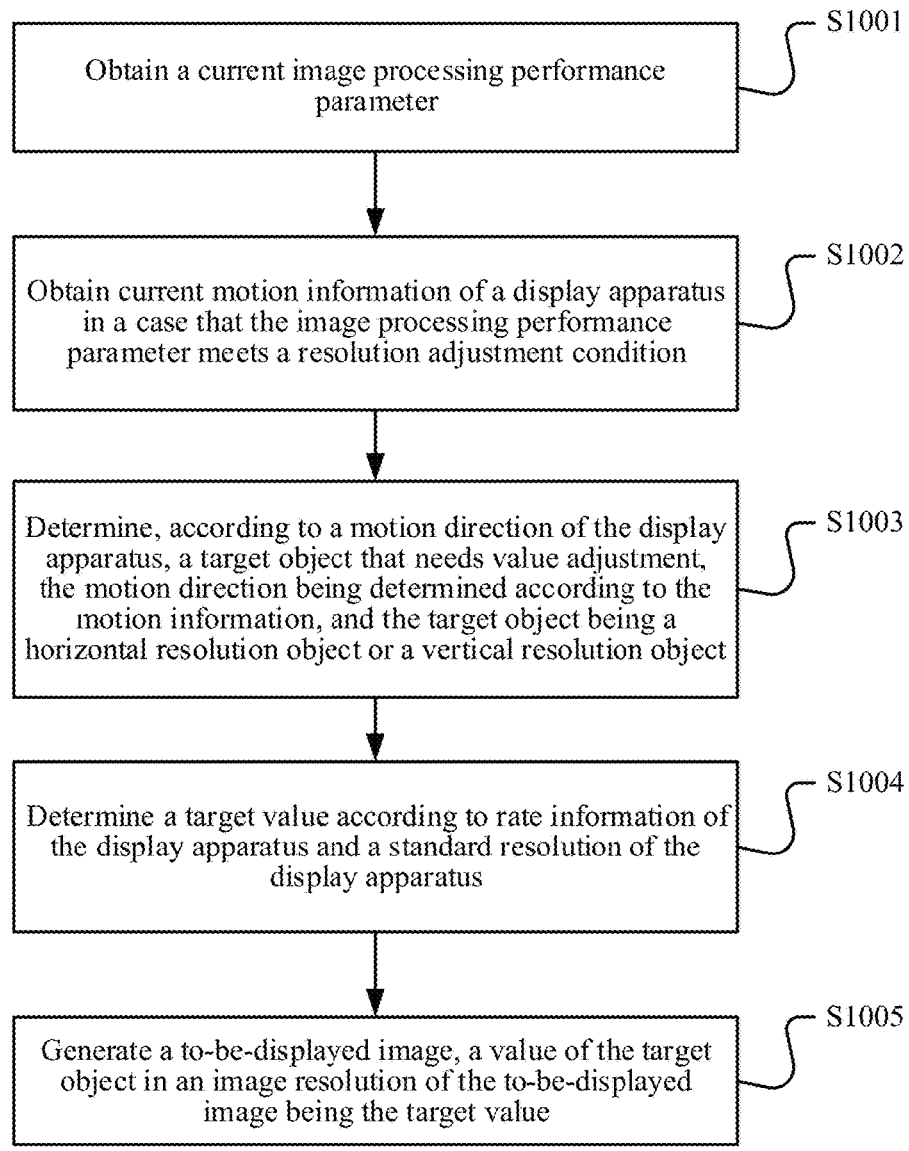
FIG. 10*a* is a schematic flowchart of another image resolution processing method according to an example embodiment of the disclosure.

FIG. 10a is a schematic flowchart of an image resolution processing method according to an example embodiment of the disclosure. The method in this embodiment of the disclosure may be performed by an image processing device. The image processing device may be specifically implemented by a computer device or formed by some structures in the computer device. For example, the image processing device may be a VR host device or an AR host device. The image processing device may alternatively be formed by some structures disposed in a wearable device having a host function and a display function. The method according to this embodiment of the disclosure includes the following operations:

S1001. Obtain a current image processing performance parameter. The image processing performance parameter refers to a parameter used for determining a current capability of generating a to-be-displayed image of the image processing device, and includes an image refresh rate of the current image processing device, an image update duration of a single frame of an image, and an image processing resource usage ratio, for example, a usage ratio of a GPU.

S1002. Obtain current motion information of a display apparatus in a case that the image processing performance parameter meets a resolution adjustment condition. The image processing performance parameter meeting the resolution adjustment condition includes any one or more of the following situations: an image refresh rate included in the image processing performance parameter is less than a preset rate threshold; an image update duration included in the image processing performance parameter is greater than a preset duration threshold; and an image processing resource usage ratio included in the image processing performance parameter is greater than a preset usage ratio threshold. That is, if the image refresh rate is relatively high, for example, not less than 90 fps, the image resolution does not need to be reduced, and image processing such as image rendering may be performed based on a standard resolution in a normal processing manner. If the image update duration is relatively short, the image resolution does not need to be reduced, and image processing such as image rendering may be performed based on the standard resolution in a normal processing manner. If the usage ratio of an image processing resource such as the GPU is relatively high, for example, if the usage ratio of the GPU is up to 98%, it is more likely that image processing cannot be normally performed, thus causing a lower refresh rate or a longer image processing duration. In this case, the image resolution needs to be reduced. The usage ratio of the image processing resource may be used as a secondary condition to determine whether to reduce the resolution used in the image processing.

S1003. Determine, according to a motion direction of the display apparatus, a target object that needs value adjustment, the motion direction being determined according to the motion information, and the target object being a horizontal resolution and/or a vertical resolution.

S1004. Determine a target value according to rate information of the display apparatus and a standard resolution of the display apparatus, the rate information being determined according to the motion information.

S1005. Generate a to-be-displayed image, a value of the target object in an image resolution of the to-be-displayed image being the target value.

In this embodiment of the disclosure, for specific implementation of operations S1002 to S1005, the description of related content in the foregoing embodiments may be referred to.

Figure 10B:
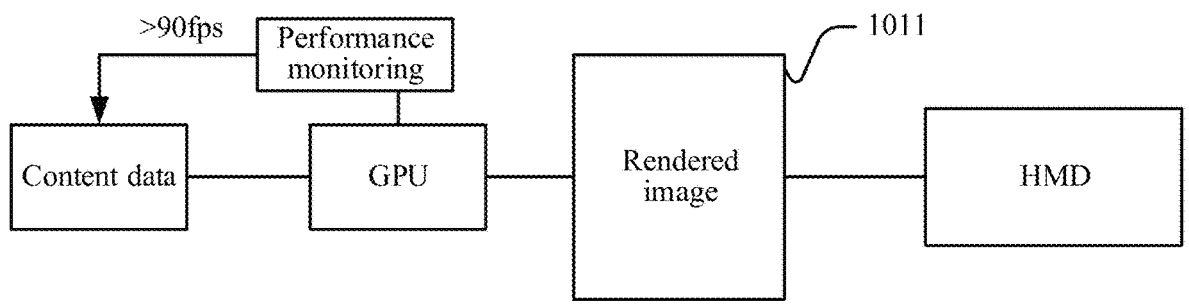
FIG. 10*b* is a schematic diagram of image processing based on a refresh rate according to an example embodiment of the disclosure.
Figure 10C:
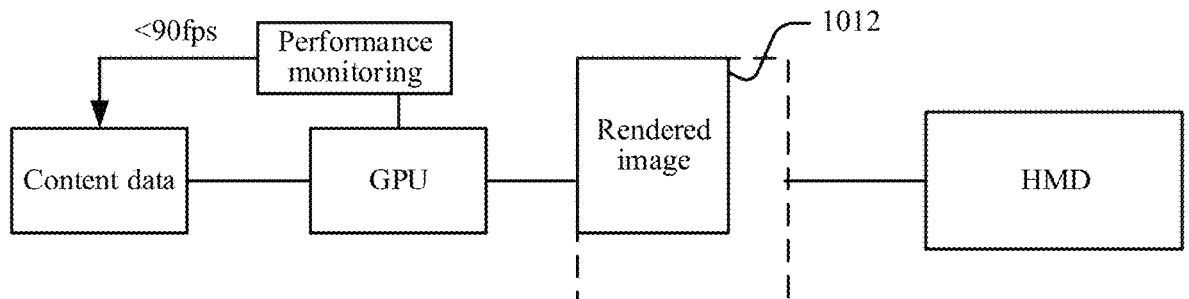
FIG. 10*c* is a schematic diagram of another image processing based on a refresh rate according to an example embodiment of the disclosure.

In an embodiment, for example, the image processing performance parameter is the image refresh rate, and the preset rate threshold is 90 fps is used. As shown in FIG. 10b, if it is determined through performance monitoring that the current image refresh rate is greater than (or equal to) 90 fps, the GPU of the image processing device outputs a rendered image 1011 having the standard resolution. As shown in FIG. 10c, if it is determined through performance monitoring that the current image refresh rate is less than 90 fps, adjustment needs to be performed based on related operations such as S1002 to S1005 mentioned above, to obtain a rendered image 1012 in which a value of a resolution corresponding to the X coordinate direction and/or the Y coordinate direction is the corresponding target value.

Figure 11:
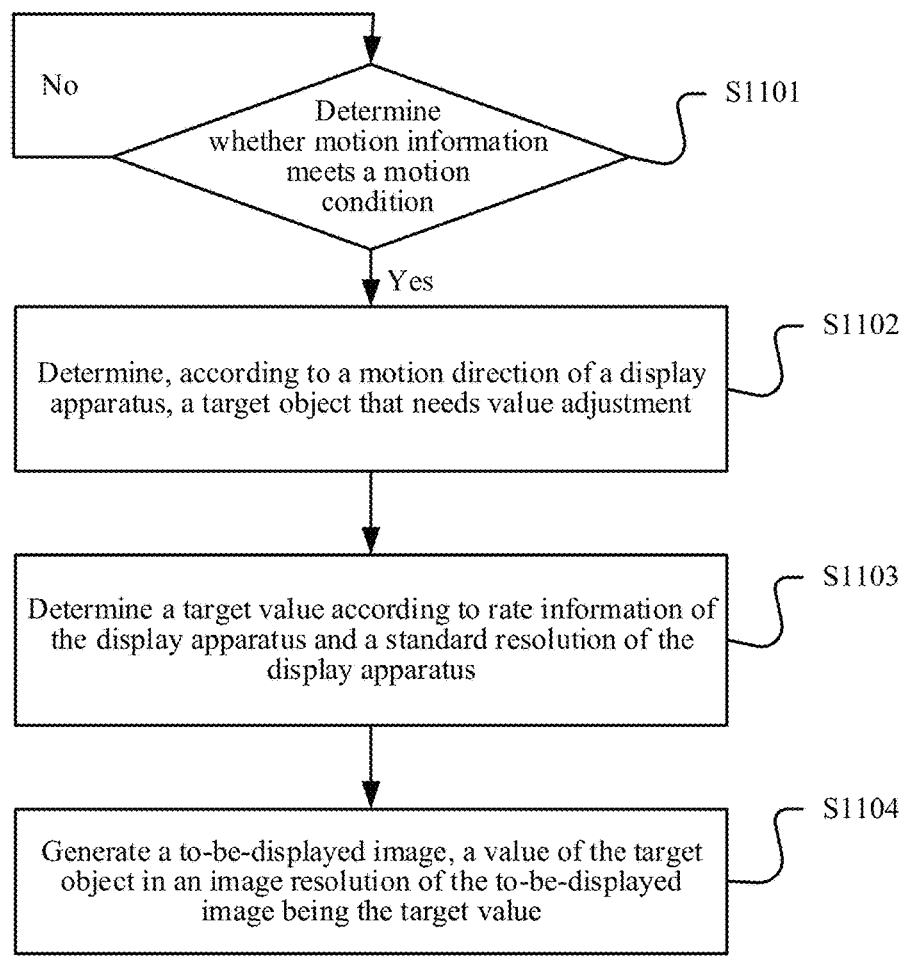
FIG. 11 is a schematic flowchart of still another image resolution processing method according to an example embodiment of the disclosure.

FIG. 11 is a schematic flowchart of still another image resolution processing method according to an example embodiment of the disclosure. The method in this embodiment of the disclosure may be performed by an image processing device. The image processing device may be specifically implemented by a computer device or formed by some structures in the computer device. For example, the image processing device may be a VR host device or an AR host device. The image processing device may alternatively be formed by some structures disposed in a wearable device having a host function and a display function. The method according to this embodiment of the disclosure includes the following operations:

S1101. Determine whether motion information meets a motion condition. The motion information mainly includes information such as the three-axis rotation state information (including the angle/angular velocity/angular acceleration), and/or the position state information (including the position/speed/acceleration) of the display apparatus mentioned above. If a determining result is yes, that is, the motion information meets the motion condition, the following S1102 is triggered to be performed. If the determining result is no, S1101 is continuously performed. That the motion information meets the motion condition includes: a motion value indicated by rate information of the display apparatus that is determined according to the motion information is greater than a preset speed threshold. In a case that the motion value of the display apparatus is greater than the speed threshold, for example, in a case that a motion acceleration value is greater than an acceleration threshold, an angular acceleration value is greater than an angular acceleration threshold, or the like, an image resolution ratio used during image processing may also be reduced. In this way, a processing load of an image processing resource such as the GPU may be reduced, and energy consumption may be reduced to a certain extent, thereby providing longer endurance power of the image processing device.

S1102. Determine, according to a motion direction of a display apparatus, a target object that needs value adjustment, the motion direction being determined according to the motion information, and the target object being a horizontal resolution and/or a vertical resolution.

S1103. Determine the target value according to the rate information of the display apparatus and a standard resolution of the display apparatus, the rate information being determined according to the motion information.

S1104. Generate a to-be-displayed image, a value of the target object in an image resolution of the to-be-displayed image being the target value.

In this embodiment of the disclosure, for specific implementation of the operations S1102 to S1104, the description of related content in the foregoing embodiments may be referred to.

In other embodiments, whether to reduce the image resolution may be comprehensively considered based on an image processing performance parameter and the motion information. In an embodiment, the current image processing performance parameter is obtained. If the image processing performance parameter meets a resolution adjustment condition (that is, a resolution needs to be adjusted), the motion information of the display apparatus is further determined, and whether the motion information meets the motion condition is determined. If the motion information meets the motion condition, S1102 to S1104 are subsequently triggered to be performed.

Figure 12:
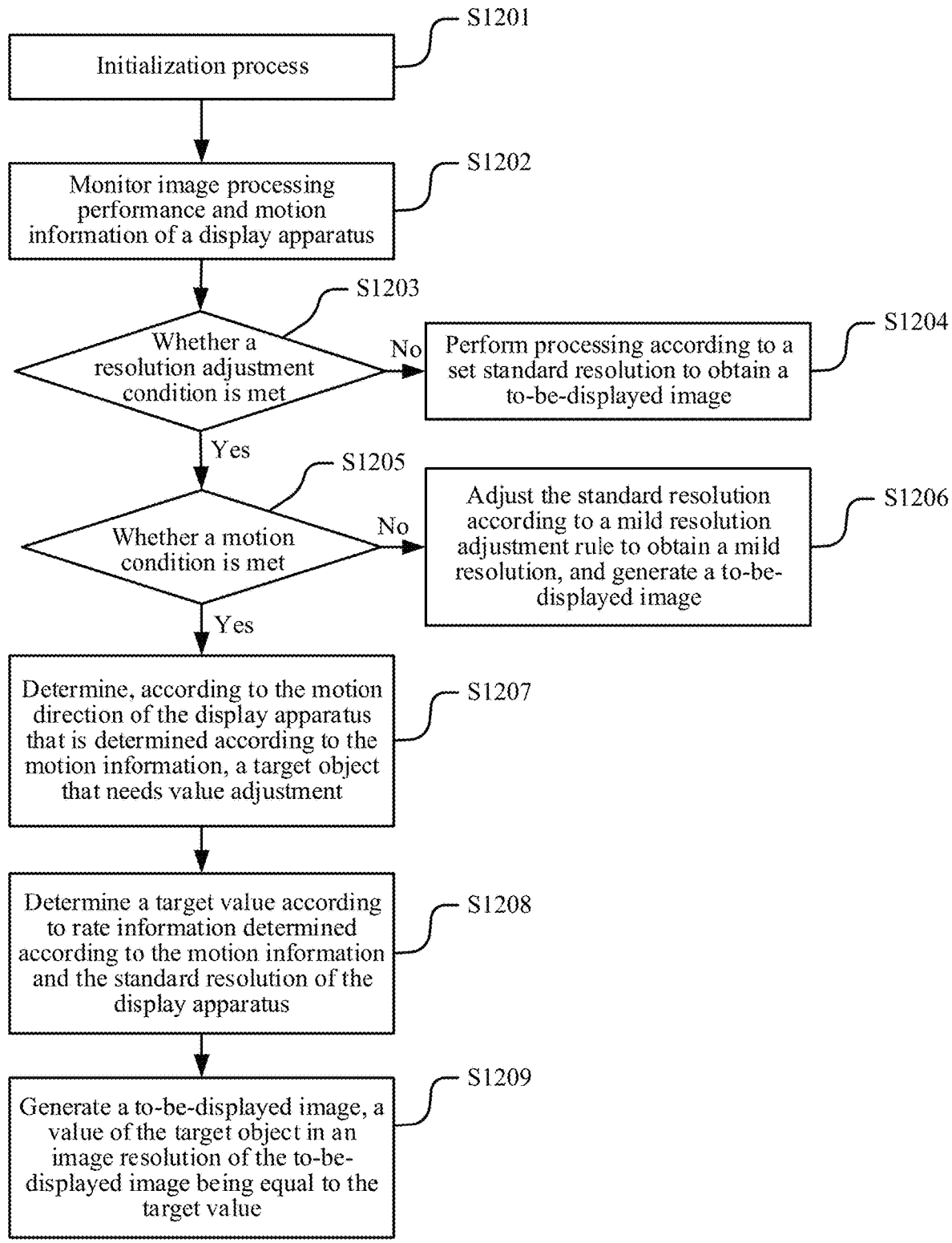
FIG. 12 is a schematic flowchart of still another image resolution processing method according to an example embodiment of the disclosure.

In an embodiment, FIG. 12 is a schematic flowchart of still another image resolution processing method according to an example embodiment of the disclosure. The method in this embodiment of the disclosure may be performed by an image processing device. The image processing device may be specifically implemented by a computer device or formed by some structures in the computer device. For example, the image processing device may be a VR host device or an AR host device. The image processing device may alternatively be formed by some structures disposed in a wearable device having a host function and a display function. The method according to this embodiment of the disclosure includes the following operations:

S1201. Perform initialization processing, including system initialization processing of an entire image processing device.

S1202. Monitor image processing performance and a motion state of a display apparatus, and obtain an image processing performance parameter and motion information of the display apparatus. Performance parameters such as an image refresh rate and data such as motion acceleration of the display apparatus are mainly determined from the GPU, so as to perform the determining operation in the following S1203.

S1203. Determine whether the image processing performance parameter meets a resolution adjustment condition, for example, a condition such as whether the refresh rate is greater than 90 fps. If a determining result is no, that is, the resolution adjustment condition is not met, S1204 is performed, so that an optimal to-be-displayed image outputted according to optimal image quality rendering settings. If the determining result is yes, that is, the resolution adjustment condition is met, the following S1205 is performed.

S1204. Perform processing according to a set standard resolution to obtain a to-be-displayed image.

S1205. Determine whether the motion information meets a motion condition, that is, determine whether a user moves rapidly. For example, the motion condition may be: acceleration included in the motion information is greater than a preset acceleration threshold, or angular acceleration is greater than a preset angular acceleration threshold, or the like. If a determining result is no, that is, the motion condition is not met, the optimal to-be-displayed image may be outputted according to the optimal image quality rendering settings, and the to-be-displayed image is directly obtained through processing based on the standard resolution. Alternatively, when the motion condition is not met, a resolution adjustment setting is performed according to a more alleviated global resolution, or the following S1206 may be performed. However, if the motion condition is met, it indicates that the motion of the display apparatus is relatively vigorous, and the following S1207 is performed.

S1206. Adjust the standard resolution according to a mild resolution adjustment rule to obtain an alleviated resolution and generate a to-be-displayed image, a resolution of the generated to-be-displayed image is the moderating resolution being the alleviated resolution, and the alleviated resolution being different from the above-mentioned target value. In an embodiment, if it is detected that the motion information does not meet the motion condition, and/or the image processing performance parameter does not meet the resolution adjustment condition, a mild resolution adjustment rule may alternatively be performed. Specific operations may include: obtaining a target ratio for performing value adjustment on the horizontal resolution and the vertical resolution; calculating a first resolution value of the horizontal resolution and a second resolution value of the vertical resolution according to the target ratio; and generating a to-be-displayed image, the to-be-displayed image having the first resolution value on the horizontal resolution and the second resolution value on the vertical resolution. The target ratio is a preset value, which is a value for slighting changing the standard resolution, for example, the value is 0.9. In this case, the first resolution value and the second resolution value are the standard resolution multiplied by 0.9, respectively. For example, the foregoing standard resolution of 1080×1200 is multiplied by 0.9 to obtain a mild resolution of 972×1080.

S1207. Determine, according to a motion direction of the display apparatus that is determined according to the motion information, a target object that needs value adjustment, the target object being a horizontal resolution and/or a vertical resolution.

S1208. Determine a target value according to rate information determined according to the motion information and the standard resolution of the display apparatus.

S1209. Generate a to-be-displayed image, a value of the target object in an image resolution of the to-be-displayed image being equal to the target value.

In this embodiment of the disclosure, for specific implementation of operations S1207 to S1209, the description of related content in the foregoing embodiments may be referred to.

In an embodiment, whether the motion information meets the motion condition may alternatively be determined first. If the motion information meets the motion condition, a current image processing performance parameter may be further obtained. In a case that the image processing performance parameter meets the resolution adjustment condition, the operation of determining, according to a motion direction of the display apparatus that is determined according to the motion information, a target object that needs value adjustment is triggered, thereby facilitating execution of subsequent operations to obtain a to-be-displayed image.

In an embodiment, after the to-be-displayed image is generated, that is, after S204, or S1005, or S1104 described above is performed, it is continuously monitored as to whether the motion information meets the motion condition, and/or the image processing performance parameter meets the resolution adjustment condition, and based on a result of continuous monitoring, the operation of determining, according to a motion direction of the display apparatus that is determined according to the motion information, a target object that needs value adjustment may be continuously performed, so as to obtain a new target value and generate a new to-be-displayed image. In addition, in a process of generating N frames of to-be-displayed images, if it is detected based on the result of continuous monitoring that no motion information meets the motion condition and/or no image processing performance parameter meets the resolution adjustment condition, the operation of determining, according to a motion direction of the display apparatus that is determined according to the motion information, a target object that needs value adjustment, or the like is stopped (or skipped). The operation of obtaining a target value is no longer executed, that is, resolution adjustment is not performed, and a to-be-displayed image whose image resolution is the standard resolution is obtained. N may be set to a value of 3 to 5, or any appropriate value as needed.

Figure 13:
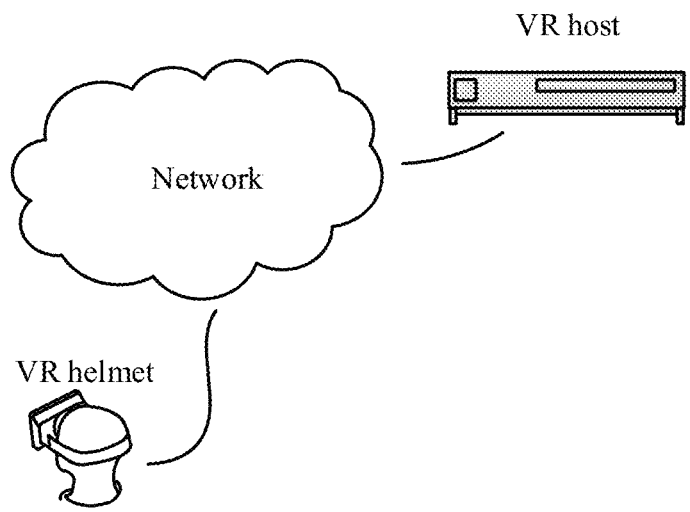
FIG. 13 is a schematic structural diagram of an image resolution processing system according to an example embodiment of the disclosure.

FIG. 13 is a schematic structural diagram of an image resolution processing system according to an example embodiment of the disclosure. The system includes an image processing device and a display apparatus. In an embodiment, the image processing device may be implemented by a computer device. The image processing device may be specifically a device such as an AR host or a VR host. FIG. 13 shows an example in which the AR host is used as the image processing device. Correspondingly, the display apparatus may be a display device, such as AR glasses or a VR helmet, used for displaying a game screen image, a computer graphics (CG) image, a high-definition image, and the like. FIG. 13 shows an example in which the VR helmet is used as the display apparatus. Processing such as image rendering is performed in the image processing device, and an image is outputted. The image is displayed in the display apparatus. The embodiment shown in FIG. 13 mainly shows an image processing scenario in which the image processing device is separated from the display apparatus. The image processing device may perform image processing through related operations described in the foregoing embodiments to finally obtain a to-be-displayed image that may be finally displayed by the display apparatus. The to-be-displayed image is outputted as a target image. The display apparatus directly displays the target image outputted by the image processing device. A network shown in FIG. 13 is merely an example. In some embodiments, the VR host and the VR helmet may alternatively be connected by other means, for example, directly connected in a wired manner through a data cable.

In an embodiment, the image resolution processing system includes an image processing device and a display apparatus. The image processing device is configured to: obtain motion information of the display apparatus; determine a motion direction and rate information of the display apparatus according to the motion information; determine, according to the motion direction, a target object that needs value adjustment, the target object being a horizontal resolution and/or a vertical resolution; determine a target value according to the rate information and a standard resolution of the display apparatus; generate a to-be-displayed image, a value of the target object in an image resolution of the to-be-displayed image being equal to the target value; and output a target image according to the to-be-displayed image. The display apparatus is configured to: transmit the motion information to the image processing device, and display the target image after receiving the target image.

In an embodiment, the display apparatus is further configured to transmit the motion information to the image processing device upon detecting that an image refresh rate of the displayed target image is less than a preset rate threshold, and/or detecting that collected motion information meets a motion condition.

Figure 14:
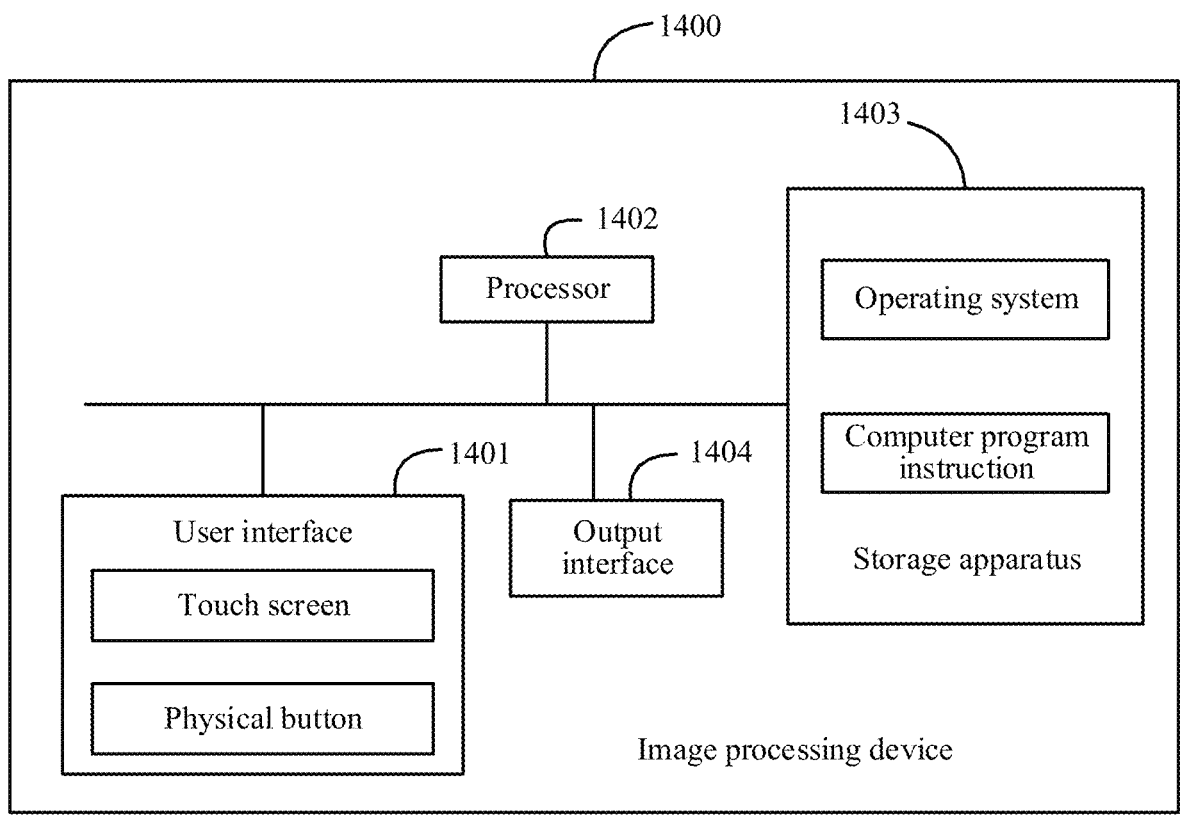
FIG. 14 is a schematic structural diagram of an image processing device according to an example embodiment of the disclosure.

In an embodiment, as shown in FIG. 14, the image processing device 1400 may include a user interface 1401, a processor 1402, a storage apparatus 1403, and an output interface 1404. The image processing device 1400 may further include a power supply module configured to supply power to the device, and a function module configured to download data including various images (for example, game data) from the Internet, and the like. The image processing device 1400 may further provide an interface module such as a speaker interface, a microphone interface, or the like.

The user interface 1401 may optionally include an interface module formed by some physical buttons, touch buttons, and the like, and may receive a user operation. The user interface 1401 may further include some structures such as a display screen that may prompt information such as a working state of the image processing device 1400 to the user. The user interface 1401 may optionally include a touch screen.

The storage apparatus 1403 may include a volatile memory, for example, a random access memory (RAM). The storage apparatus 1403 may alternatively include a non-volatile memory, for example, a flash memory, and a solid-state drive (SSD). The storage apparatus 1403 may alternatively include a combination of the foregoing types of memories.

The processor 1402 may be a central processing unit (CPU) 1402. The processor 1402 may further include a hardware chip. The foregoing hardware chip may be an application-specific integrated circuit (ASIC), a programmable logic device (PLD), or the like. The PLD may be a field programmable gate array (FPGA), generic array logic (GAL), or the like. The processor 1402 may alternatively be a combination of the foregoing structures.

In an embodiment, the storage apparatus 1403 is further configured to store computer program instructions. The processor 1402 may invoke the computer program instructions, and may perform the foregoing various methods and operations.

The processor 1402 invokes the computer program instructions stored in the storage apparatus 1403 to obtain motion information of the display apparatus; determine a motion direction and rate information of the display apparatus according to the motion information; determine, according to the motion direction, a target object that needs value adjustment, the target object being a horizontal resolution and/or a vertical resolution; determine a target value according to the rate information and a standard resolution of the display apparatus; and generate a to-be-displayed image, a value of the target object in an image resolution of the to-be-displayed image being equal to the target value. Generated display images may be outputted through the output interface 1404, so that the images are displayed by the display apparatus. In other embodiments, if the image processing device 1400 includes a display screen, the to-be-displayed image generated by the processor 1402 is transmitted to the display screen through the output interface 1404, and is directly displayed by the display screen.

In an embodiment, before obtaining the motion information of the display apparatus, the processor 1402 is further configured to: obtain a current image processing performance parameter; and in a case that the image processing performance parameter meets a resolution adjustment condition, trigger the operation of obtaining motion information of the display apparatus. The image processing performance parameter meeting the resolution adjustment condition includes at least one of the following situations: an image refresh rate included in the image processing performance parameter is less than a preset rate threshold; an image update duration included in the image processing performance parameter is greater than a preset duration threshold; and an image processing resource usage ratio included in the image processing performance parameter is greater than a preset usage ratio threshold.

In an embodiment, the processor 1402 is further configured to: in a case that the motion information meets the motion condition, trigger the operation of determining, according to the motion direction of the display apparatus, a target object that needs value adjustment. The motion information meeting the motion condition includes: a motion value indicated by the rate information of the display apparatus that is determined according to the motion information is greater than a preset speed threshold.

In an embodiment, the processor 1402 is further configured to: determine, by using a resolution ratio determining rule, a resolution ratio corresponding to the motion information; and obtain the target value according to a value of the target object in the standard resolution and the resolution ratio.

In an embodiment, the processor 1402 is further configured to: determine, by using a regulation value determining rule, a regulation value corresponding to an image update duration included in a current image processing performance parameter; and determine, by using a resolution ratio determining rule, a resolution ratio corresponding to the motion information; and obtain the target value according to the value of the target object in the standard resolution, the regulation value, and the resolution ratio.

In an embodiment, the resolution ratio determining rule includes: in a case that a motion value corresponding to the rate information of the display apparatus is less than a first threshold, determining that the resolution ratio corresponding to the motion information is a first fixed ratio. In addition, the resolution ratio is not less than a second fixed ratio.

In an embodiment, the resolution ratio determining rule includes: in a case that the image update duration included in the current image processing performance parameter is less than a first duration threshold, determining that the regulation value is a first fixed regulation value. In addition, the regulation value is not less than a second fixed regulation value.

In an embodiment, the processor 1402 invokes computer program instructions stored in the storage apparatus 1403, and is configured to further determine a target image object from the generated to-be-displayed image, and adjust geometric fineness of the target image object according to a geometric fineness adjustment rule.

In an embodiment, the processor 1402 invokes the computer program instructions stored in the storage apparatus 1403, to further: magnify the to-be-displayed image according to a display resolution value of the display apparatus and a resolution value of the to-be-displayed image; and output the magnified to-be-displayed image to the display apparatus for display.

For specific function implementation of the processor 1402 in this embodiment of the disclosure, the description of related content in the foregoing embodiments may be referred to. Details are not repeated herein.

In this embodiment of the disclosure, when motion of a user is detected, a resolution value in an X axis and/or a Y axis in an image coordinate system is adjusted according to a motion direction. A certain refresh rate is ensured by changing the resolution value of the image in a processing process such as image rendering, and stability of an image displayed by a device such as a head-mounted display apparatus may be maintained.

Figure 15:
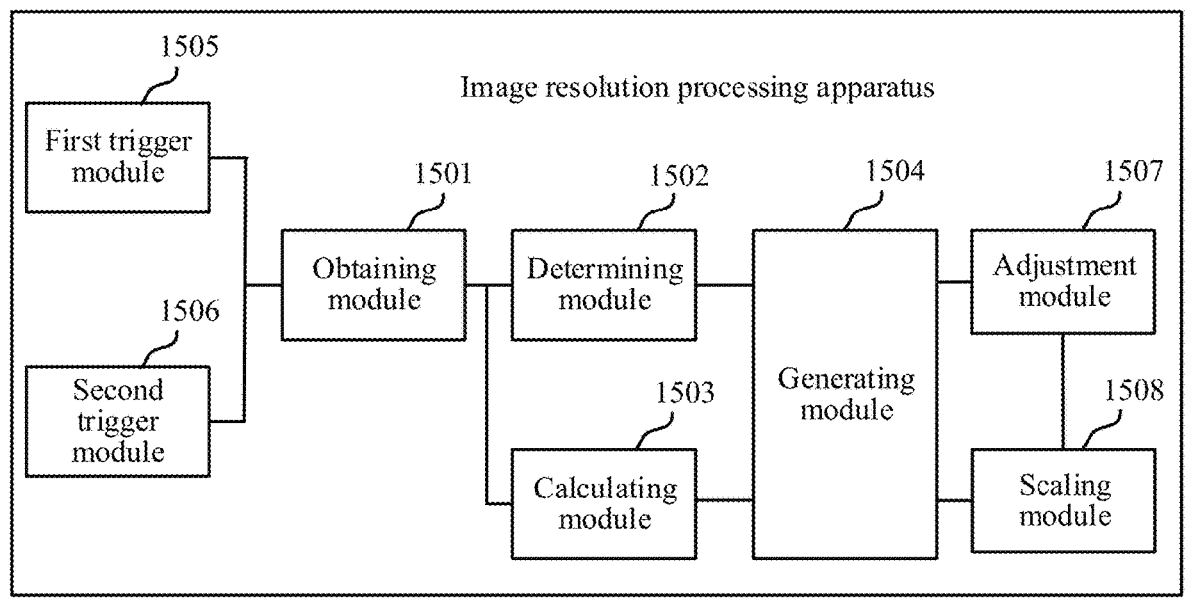
FIG. 15 is a schematic structural diagram of an image resolution processing apparatus according to an example embodiment of the disclosure.

FIG. 15 is a schematic structural diagram of an image resolution processing apparatus 1500 according to an example embodiment of the disclosure. The apparatus in this embodiment of the disclosure may be disposed in a device such as VR host or an AR host according to a requirement. The apparatus in this embodiment of the disclosure may alternatively be disposed in a device such as a smartphone, a tablet computer, or an intelligent wearable device that may provide a host function. The apparatus in this embodiment of the disclosure includes the following modules.

An obtaining module 1501 is configured to: obtain motion information of a display apparatus, and determine a motion direction and rate information of the display apparatus according to the motion information. A determining module 1502 is configured to determine, according to the motion direction, a target object that needs value adjustment, the target object being a horizontal resolution and/or a vertical resolution. A calculating module 1503 is configured to determine a target value according to the rate information and a standard resolution of the display apparatus. A generating module 1504 is configured to generate a to-be-displayed image, a value of the target object in an image resolution of the to-be-displayed image being equal to the target value.

In an embodiment, the image resolution processing apparatus 1500 further includes a first trigger module 1505. The first trigger module 1505 is configured to: obtain a current image processing performance parameter; and in a case that the image processing performance parameter meets a resolution adjustment condition, trigger the obtaining module 1501 to obtain the motion information of the display apparatus. The image processing performance parameter meeting the resolution adjustment condition includes at least one of the following situations: an image refresh rate included in the image processing performance parameter is less than a preset rate threshold; an image update duration included in the image processing performance parameter is greater than a preset duration threshold; and an image processing resource usage ratio included in the image processing performance parameter is greater than a preset usage ratio threshold.

In an embodiment, the image resolution processing apparatus 1500 further includes a second trigger module 1506. The second trigger module 1506 is configured to: in a case that the motion information meets a motion condition, trigger the obtaining module 1501 to determine, according to the motion direction of the display apparatus that is determined according to the motion information, the target object that needs value adjustment. The motion information meeting the motion condition includes: a motion value indicated by the rate information of the display apparatus that is determined according to the motion information is greater than a preset speed threshold.

In an embodiment, trigger functions of the first trigger module 1505 and the second trigger module 1506 may be implemented by the same trigger module.

In an embodiment, the calculating module 1503 is specifically configured to: determine, by using a resolution ratio determining rule, a resolution ratio corresponding to the motion information; and obtain the target value according to a value of the target object in the standard resolution and the resolution ratio.

In an embodiment, the calculating module 1503 is specifically configured to: determine, by using a regulation value determining rule, a regulation value corresponding to an image update duration included in a current image processing performance parameter; determine, by using a resolution ratio determining rule, a resolution ratio corresponding to the motion information; and obtain the target value according to the value of the target object in the standard resolution, the regulation value, and the resolution ratio.

In an embodiment, the resolution ratio determining rule includes: in a case that a motion value corresponding to the rate information of the display apparatus is less than a first threshold, determining that the resolution ratio corresponding to the motion information is a first fixed ratio. In addition, the resolution ratio is not less than a second fixed ratio.

In an embodiment, the resolution ratio determining rule includes: in a case that the image update duration included in the current image processing performance parameter is less than a first duration threshold, determining that the regulation value is a first fixed regulation value. In addition, the regulation value is not less than a second fixed regulation value.

In an embodiment, the image resolution processing apparatus 1500 may further include an adjustment module 1507. The adjustment module 1507 is configured to: determine a target image object from the generated to-be-displayed image, and adjust geometric fineness of the target image object according to a geometric fineness adjustment rule.

In an embodiment, the image resolution processing apparatus 1500 may further include a scaling module 1508. The scaling module 1508 is configured to: magnify the to-be-displayed image according to a display resolution value of the display apparatus and a resolution value of the to-be-displayed image; and output the magnified to-be-displayed image to the display apparatus for display.

In an embodiment, specific functions of the adjustment module 1507 and the scaling module 1508 may be implemented by one processing module. In an embodiment, the to-be-displayed image outputted by the generating module 1504 may be transmitted directly to the scaling module 1508. The scaling module 1508 may directly perform magnification without adjusting the geometric fineness of the target image object according to the geometric fineness adjustment rule.

For specific function implementation of the function modules of the image resolution processing apparatus according to this embodiment of the disclosure, the description of related content in the foregoing embodiments may be referred to. Details are not repeated herein.

In this embodiment of the disclosure, when motion of a user is detected, a resolution value in an X axis and/or a Y axis in an image coordinate system is adjusted according to a motion direction. A certain refresh rate is ensured by changing the resolution value of the image in a processing process such as image rendering, and stability of an image displayed by a device such as a head-mounted display apparatus may be maintained.

In an embodiment, the image resolution processing apparatus provided in the disclosure may be implemented in a form of a computer program, and the computer program may run on the image processing device shown in FIG. 14. The memory of the image processing device may store program modules forming the image resolution processing apparatus, for example, the obtaining module, the determining module, the calculating module, and the generating module shown in FIG. 15. The computer program formed by the program modules causes the processor to perform the operations in the image resolution processing method in the embodiments of the disclosure described in this specification.

For example, the image processing device shown in FIG. 14 may perform operation S201 by using the obtaining module in the image resolution processing apparatus shown in FIG. 15. The image processing device may perform operation S202 by using the determining module. The image processing device may perform operation S203 by using the calculating module. The image processing device may perform operation S204 by using the generating module.

In an embodiment, an image processing device is provided, including a processor and a memory. The memory stores a computer program, and the computer program, when executed by the processor, causes the processor to perform the operations of the foregoing image resolution processing method. The operations of the image resolution processing method herein may be the operations of the image resolution processing method in the foregoing embodiments.

In an embodiment, a computer-readable storage medium is provided, storing a computer program, the computer program, when executed by a processor, causing the processor to perform the operations of the foregoing image resolution processing method. The operations of the image resolution processing method herein may be the operations of the image resolution processing method in the foregoing embodiments.

A person of ordinary skill in the art may understand that all or some of the processes of the methods in the foregoing embodiments may be implemented by a computer program instructing relevant hardware. The program may be stored in a computer-readable storage medium. During execution of the program, processes of the foregoing method embodiments may be included. The storage medium may be a magnetic disk, an optical disc, a read-only memory (ROM) or a random access memory (RAM), or the like.

Operations and modules in the procedures and the structural diagrams described above may not be all necessary, and some operations or modules may be omitted depending on embodiments. An execution sequence of the operations is not fixed and may be adjusted as needed. Division of the modules is merely functional division for ease of descriptions. In an actual implementation of an example embodiment of the disclosure, one module may include a plurality of modules, and functions of a plurality of modules may be implemented by a same module. These modules may be located in a same device or in different devices.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

The foregoing descriptions are merely some embodiments of the disclosure, and certainly are not intended to limit the protection scope of the disclosure. A person of ordinary skill in the art may understand all or some processes of the foregoing embodiments, and equivalent modifications made according to the claims of the disclosure shall still fall within the scope of the disclosure.

What is claimed is:

1. An image resolution processing method, executed by an image processing device, the method comprising:
   obtaining motion information of a display apparatus;
   determining a motion direction and rate information of the display apparatus based on the motion information, the motion direction including at least one of a horizontal direction and a vertical direction;
   determining a target object that is a horizontal resolution based on the motion direction being in the horizontal direction, determining the target object that is a vertical resolution based on the motion direction being the vertical direction, and determining the target object that is the horizontal resolution and the vertical resolution based on the motion direction being a diagonal direction;

determining a target value based on the rate information and a standard resolution of the display apparatus; and generating a to-be-displayed image, a value of the target object in an image resolution of the to-be-displayed image being equal to the target value, wherein the determining the target value comprises:

determining, by using a resolution ratio determining rule, a resolution ratio corresponding to the motion information; and obtaining the target value according to a value of the target object in the standard resolution and the resolution ratio, wherein the resolution ratio determining rule is defined in a manner such that, based on a motion value (b) corresponding to the rate information being equal to or greater than a first threshold and less than a second threshold, the resolution ratio (a) corresponding to the motion information is determined by using an equation a=kb, and wherein a plurality of coordinate points of a motion value and a resolution ratio are obtained, via testing, based on visually acceptable degrees of an image blur in motion with respect to a plurality of users, and the slope k is obtained based on the plurality of coordinate points between the first threshold and the second threshold of the motion value.

2. The method according to claim 1, wherein the obtaining the motion information comprises:

obtaining an image processing performance parameter; and triggering the obtaining of the motion information in response to at least one of the following conditions being met:

an image refresh rate included in the image processing performance parameter is less than a preset rate threshold;

an image update duration included in the image processing performance parameter is greater than a preset duration threshold; and an image processing resource usage ratio included in the image processing performance parameter is greater than a preset usage ratio threshold.

3. The method according to claim 1, wherein the determining the target object comprises triggering the determining the target object based on a motion value indicated by the rate information of the display apparatus being greater than a preset speed threshold.

4. The method according to claim 1, wherein the determining the target value further comprises:

determining, by using a regulation value determining rule, a regulation value corresponding to an image update duration included in an image processing performance parameter;

obtaining the target value according to a value of the target object in the standard resolution, the regulation value, and the resolution ratio.

5. The method according to claim 4, wherein the regulation value determining rule is such that, the image update duration included in the image processing performance parameter being less than a first duration threshold, the regulation value is determined to be a first fixed regulation value, the first fixed regulation value being not less than a second fixed regulation value.

6. The method according to claim 1, further comprising: determining a target image object from the generated to-be-displayed image, and adjusting geometric fineness of the target image object according to a geometric fineness adjustment rule.

7. The method according to claim 1, further comprising: magnifying the to-be-displayed image according to a display resolution of the display apparatus and the image resolution of the to-be-displayed image; and outputting the magnified to-be-displayed image to the display apparatus.

8. The method according to claim 1, wherein the resolution ratio determining rule is further defined in a manner such that: (i) based on the motion value corresponding to the rate information of the display apparatus being less than the first threshold, the resolution ratio corresponding to the motion information is determined to be a first fixed ratio, the first fixed ratio being not less than a second fixed ratio, (ii) based on the motion value corresponding to the rate information being equal to or greater than the second threshold, the resolution ratio corresponding to the motion information is determined to be the second fixed ratio.

9. A non-transitory computer-readable storage medium, storing computer readable instructions executable by one or more processors to perform the method according to claim 1.

10. A device, comprising at least one memory and at least one processor, the at least one memory storing computer-readable instructions, and the computer-readable instructions, when executed by the at least one processor, causing the at least one processor to perform the method according to claim 1.

11. An image resolution processing system, comprising:

an image processing device comprising at least one processor configured to:

obtain motion information of a display apparatus;

determine a motion direction and rate information of the display apparatus based on the motion information, the motion direction including at least one of a horizontal direction and a vertical direction;

determine a target object that is a horizontal resolution based on the motion direction being in the horizontal direction, determine the target object that is a vertical resolution based on the motion direction being the vertical direction, and determine the target object that is the horizontal resolution and the vertical resolution based on the motion direction being a diagonal direction;

determine a target value based on the rate information and a standard resolution of the display apparatus;

generate a to-be-displayed image, a value of the target object in an image resolution of the to-be-displayed image being equal to the target value; and output a target image based on the to-be-displayed image; and the display apparatus is configured to: transmit the motion information to the image processing device, and display the target image after receiving the target image, wherein the at least one processor is configured to determine the target value by:

determining, by using a resolution ratio determining rule, a resolution ratio corresponding to the motion information; and obtaining the target value according to a value of the target object in the standard resolution and the resolution ratio, wherein the resolution ratio determining rule is defined in a manner such that, based on a motion value (b)

corresponding to the rate information being equal to or greater than a first threshold and less than a second threshold, the resolution ratio (a) corresponding to the motion information is determined by using an equation a=kb, and wherein a plurality of coordinate points of a motion value and a resolution ratio are obtained, via testing, based on visually acceptable degrees of an image blur in motion with respect to a plurality of users, and the slope k is obtained based on the plurality of coordinate points between the first threshold and the second threshold of the motion value.

12. The system according to claim 11, wherein the display apparatus is further configured to transmit the motion information to the image processing device upon detecting that an image refresh rate of the displayed target image is less than a preset rate threshold, and/or detecting that the motion information meets a certain condition.

13. An image resolution processing apparatus, comprising:
at least one memory configured to store program code; and
at least one processor configured to read the program code and operate as instructed by the program code, the program code comprising:
obtaining code configured to cause at least one of the at least one processor to obtain motion information of a display apparatus, and determine a motion direction and rate information of the display apparatus based on the motion information, the motion direction including at least one of a horizontal direction and a vertical direction;
determining code configured to cause at least one of the at least one processor to determine a target object that is a horizontal resolution based on the motion direction being in the horizontal direction, determine the target object that is a vertical resolution based on the motion direction being the vertical direction, and determine the target object that is the horizontal resolution and the vertical resolution based on the motion direction being a diagonal direction;
calculating code configured to cause at least one of the at least one processor to determine a target value based on the rate information and a standard resolution of the display apparatus; and
generating code configured to cause at least one of the at least one processor to generate a to-be-displayed image, a value of the target object in an image resolution of the to-be-displayed image being equal to the target value,
wherein the calculating code further causes at least one of the at least one processor to:
determine, by using a resolution ratio determining rule, a resolution ratio corresponding to the motion information; and
obtain the target value according to a value of the target object in the standard resolution and the resolution ratio,
wherein the resolution ratio determining rule is defined in a manner such that, based on a motion value (b) corresponding to the rate information being equal to or greater than a first threshold and less than a second threshold, the resolution ratio (a) corresponding to the motion information is determined by using an equation a=kb, and wherein a plurality of coordinate points of a motion value and a resolution ratio are obtained, via testing, based on visually acceptable degrees of an image blur in motion with respect to a plurality of users, and the slope k is obtained based on the plurality of coordinate points between the first threshold and the second threshold of the motion value.

14. The apparatus according to claim 13, wherein the program code further comprises:
code configured to cause at least one of the at least one processor to obtain an image processing performance parameter, and triggering an operation of the obtaining code in response to at least one of the following conditions being met:
an image refresh rate included in the image processing performance parameter is less than a preset rate threshold;
an image update duration included in the image processing performance parameter is greater than a preset duration threshold; and
an image processing resource usage ratio included in the image processing performance parameter is greater than a preset usage ratio threshold.

15. The apparatus according to claim 13, wherein the program code further comprises code configured to cause at least one of the at least one processor to trigger an operation of the determining code based on a motion value indicated by the rate information of the display apparatus being greater than a preset speed threshold.

16. The apparatus according to claim 13, wherein the calculating code further causes at least one of the at least one processor to: determine, by using a regulation value determining rule, a regulation value corresponding to an image update duration included in an image processing performance parameter; and obtain the target value according to a value of the target object in the standard resolution, the regulation value, and the resolution ratio.

17. The apparatus according to claim 13, wherein the program code further comprises:
code configured to cause at least one of the at least one processor to determine a target image object from the generated to-be-displayed image, and adjust geometric fineness of the target image object according to a geometric fineness adjustment rule.

18. The apparatus according to claim 13, wherein the program code further comprises:
code configured to cause at least one of the at least one processor to magnify the to-be-displayed image according to a display resolution of the display apparatus and the image resolution of the to-be-displayed image; and output the magnified to-be-displayed image to the display apparatus.

* * * * *